US010071213B2

(12) United States Patent
Acker et al.

(10) Patent No.: US 10,071,213 B2
(45) Date of Patent: *Sep. 11, 2018

(54) SYSTEMS AND METHOD FOR DELIVERY OF THERAPEUTIC GAS TO PATIENTS, IN NEED THEREOF, RECEIVING BREATHING GAS FROM A VENTILATOR THAT VARIES AT LEAST PRESSURE AND/OR FLOW USING ENHANCED THERAPEUTIC GAS (NO) FLOW MEASUREMENT

(71) Applicant: Mallinckrodt Hospital Products IP Limited, Dublin (IE)

(72) Inventors: Jaron M. Acker, Madison, WI (US); Craig R. Tolmie, Stoughton, WI (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 612 days.

This patent is subject to a terminal disclaimer.

(21) Appl. No.: 14/700,594

(22) Filed: Apr. 30, 2015

(65) Prior Publication Data
US 2015/0314101 A1 Nov. 5, 2015

Related U.S. Application Data

(60) Provisional application No. 61/987,852, filed on May 2, 2014.

(51) Int. Cl.
*A61M 16/00* (2006.01)
*A61M 16/12* (2006.01)
(Continued)

(52) U.S. Cl.
CPC ........ *A61M 16/00* (2013.01); *A61M 16/0003* (2014.02); *A61M 16/0057* (2013.01);
(Continued)

(58) Field of Classification Search
CPC ............... A61M 16/0003–16/0012; A61M 2016/0027–2016/0042;
(Continued)

(56) References Cited

U.S. PATENT DOCUMENTS 5,531,218 A 7/1996 Krebs
5,558,083 A 9/1996 Bathe et al.
(Continued)

FOREIGN PATENT DOCUMENTS

EP 0621051 10/1994
EP 0977609 8/2002
WO WO-2012/094008 7/2012

OTHER PUBLICATIONS

PCT International Search Report and Written Opinion in PCT/US2015/028738, dated Jul. 28, 2015, 10 pages.
(Continued)

*Primary Examiner* — Steven Douglas

(57) ABSTRACT

The present disclosure generally relates to systems and methods for delivery of therapeutic gas to patients, in need thereof, receiving breathing gas from a high frequency ventilator using at least enhanced therapeutic gas (e.g., nitric oxide, NO, etc.) flow measurement. At least some of these enhanced therapeutic gas flow measurements can be used to address some surprising phenomenon that may, at times, occur when wild stream blending therapeutic gas into breathing gas a patient receives from a breathing circuit affiliated with a high frequency ventilator. Utilizing at least some of these enhanced therapeutic gas flow measurements the dose of therapeutic gas wild stream blended into breathing gas that the patient receives can at least be more accurate and/or under delivery of therapeutic gas into the breathing gas can be avoided and/or reduced.

25 Claims, 6 Drawing Sheets

(51) Int. Cl.
*A61M 16/06* (2006.01)
*A61M 16/20* (2006.01)
*G01N 33/00* (2006.01)

(52) U.S. Cl.
CPC ............ *A61M 16/06* (2013.01); *A61M 16/12* (2013.01); *A61M 16/122* (2014.02); *A61M 16/201* (2014.02); *G01N 33/0037* (2013.01); *A61M 2016/003* (2013.01); *A61M 2016/0039* (2013.01); *A61M 2202/0275* (2013.01); *A61M 2202/0283* (2013.01); *A61M 2205/15* (2013.01); *A61M 2205/3334* (2013.01); *A61M 2205/35* (2013.01)

(58) Field of Classification Search
CPC .......... A61M 16/00–16/22; A61M 2202/0275; A61M 2202/0283; A61M 2205/15; A61M 2205/3334; A61M 2205/35; A61M 16/122; A61M 16/0057; A61M 16/201; A61M 2016/003; G01N 33/0037
See application file for complete search history.

(56) References Cited

U.S. PATENT DOCUMENTS

| | | | |
|---|---|---|---|
| 5,732,693 A | 3/1998 | Bathe et al. | |
| 5,732,694 A | 3/1998 | Bathe et al. | |
| 5,752,504 A | 5/1998 | Bathe | |
| 6,125,846 A | 10/2000 | Bathe et al. | |
| 6,786,217 B2 * | 9/2004 | Stenzler | A61M 16/12 128/204.18 |
| 7,523,752 B2 | 4/2009 | Montgomery et al. | |
| 8,282,966 B2 | 10/2012 | Baldassarre et al. | |
| 8,291,904 B2 | 10/2012 | Bathe et al. | |
| 8,293,284 B2 | 10/2012 | Baldassarre et al. | |
| 8,431,163 B2 | 4/2013 | Baldassarre et al. | |
| 8,573,209 B2 | 11/2013 | Bathe et al. | |
| 8,573,210 B2 | 11/2013 | Bathe et al. | |
| 8,776,794 B2 | 7/2014 | Bathe et al. | |
| 8,776,795 B2 | 7/2014 | Bathe et al. | |
| 8,795,741 B2 | 8/2014 | Baldassarre | |
| 8,846,112 B2 | 9/2014 | Baldassarre | |
| 2005/0172966 A1 * | 8/2005 | Blaise | A61M 16/12 128/204.21 |
| 2007/0034208 A1 | 2/2007 | Roel et al. | |
| 2010/0252037 A1 * | 10/2010 | Wondka | A61M 16/0666 128/203.12 |
| 2013/0118486 A1 * | 5/2013 | Schnitman | A61M 16/0051 128/202.22 |
| 2015/0273175 A1 | 10/2015 | Acker et al. | |

OTHER PUBLICATIONS

INOmax DS (Delivery System): Operation Manual (800 ppm INOMAX (nitric oxide) for Inhalation), Ikaria, Inc. 2010, 112 pages.
INOvent Delivery System: Operation and Maintenance Manual (CGA Variant), Datex-Ohmeda, Inc. 2000, 180 pages.
Using the INOpulse DS Subject Guide, Ikaria, Inc. 2012, 50 pages.
INOmax Label, Nitric Oxide Gas, INO Therapeutics 2013, 2 pages.
INOmax DSIR (Delivery System): Operation Manual (800 ppm INOMAX (nitric oxide) for Inhalation), Ikaria, Inc. 2012, 136 pages.

* cited by examiner

SYSTEMS AND METHOD FOR DELIVERY OF THERAPEUTIC GAS TO PATIENTS, IN NEED THEREOF, RECEIVING BREATHING GAS FROM A VENTILATOR THAT VARIES AT LEAST PRESSURE AND/OR FLOW USING ENHANCED THERAPEUTIC GAS (NO) FLOW MEASUREMENT

CROSS-REFERENCE

This application claims the benefit under 35 U.S.C. § 119(e) to U.S. Provisional Application No. 61/987,852, filed May 2, 2014, the entire contents of which are incorporated herein by reference in their entirety.

FIELD

The present invention generally relates to systems and methods for delivery of therapeutic gas to patients, in need thereof, receiving breathing gas from a ventilator that varies at least pressure and/or flow using enhanced therapeutic gas (NO) flow measurement.

BACKGROUND

Therapeutic gas can be delivered to patients, in need thereof, to provide medical benefits. One such therapeutic gas is nitric oxide (NO) gas that, when inhaled, acts to dilate blood vessels in the lungs, improving oxygenation of the blood and reducing pulmonary hypertension. Because of at least this, nitric oxide can be provided as a therapeutic gas in the inspiratory breathing gases for patients with pulmonary hypertension.

Further, many patients receive breathing gas (e.g., inspiratory breathing gas) from a ventilator that can at least vary pressure and/or flow (e.g., high frequency ventilator, etc.). Unlike conventional ventilators, high frequency ventilators use a constant distending pressure (mean airway pressure [MAP]) with pressure variations oscillating around the MAP at very high rates (e.g., up to 900 cycles per minute, etc.). In other words, high frequency ventilators maintain a constant pressure within the patient breathing circuit and this pressure oscillates at very high rates. Beneficially, this can encourage gas exchange across blood vessels in the patient's lungs.

Although high frequency ventilators can be beneficial, patients receiving breathing gas from high frequency ventilators may receive additional benefits from therapeutic gas. To take advantage of these additional benefits the therapeutic gas may need to be delivered into breathing gas that the patient receives from a breathing circuit affiliated with the high frequency ventilator. However, delivering therapeutic gas into patient breathing gas being delivered to a patient from a high frequency ventilator can be difficult and/or present unforeseen problems. These difficulties and/or unforeseen problems can impact the accuracy of therapeutic gas delivery and/or dosing.

Accordingly, a need exists to overcome the difficulties and/or unforeseen problems that can occur when delivering therapeutic gas to a patient receiving breathing gas from a ventilator that can at least vary pressure and/or flow (e.g., high frequency ventilator, etc.) to increase accuracy of therapeutic gas delivery and/or dosing.

SUMMARY

Aspects of the present invention relate to a nitric oxide delivery system for delivering therapeutic gas comprising NO into the inspiratory limb of a breathing circuit, which may be affiliated with a high frequency ventilator. The nitric oxide delivery system may comprise an injector module for receiving a flow of therapeutic gas and injecting the therapeutic gas into the delivery circuit. The injector module may include and/or can be in communication with a mono-directional NO flow sensor capable of measuring forward NO flow (e.g., going into the injector module, from the nitric oxide delivery system to the injector module, etc.) and/or a bi-directional NO flow sensor capable of measuring forward NO flow and reverse NO flow. Using the above flow sensor and/or information communicated from the flow sensor to the nitric oxide delivery system, the nitric oxide delivery system can deliver NO to the injector module more accurately and/or under delivery of therapeutic gas into the breathing gas can be avoided and/or reduced.

In exemplary embodiments, the NO flow sensor can be used to address at least false flow phenomena surprisingly found by applicant.

In exemplary embodiments, the flow information can be from the bi-directional flow sensor. This information from the bi-directional NO flow sensor can be used to detect use of a ventilator that can at least vary pressure and/or flow (e.g., high frequency ventilator, etc.) and/or compensate for distortions in the flow information generated by at least the ventilator.

In exemplary embodiments, the flow information can be from the mono-directional flow sensor. This information from the mono-directional flow sensor can be used to detect use of a ventilator that can at least vary pressure and/or flow (e.g., high frequency ventilator, etc.) and/or compensate for distortions in the flow information generated by at least the ventilator.

BRIEF DESCRIPTION OF THE DRAWINGS

The features and advantages of the present invention will be more fully understood with reference to the following, detailed description when taken in conjunction with the accompanying figures, wherein.

DETAILED DESCRIPTION

Figure 1:
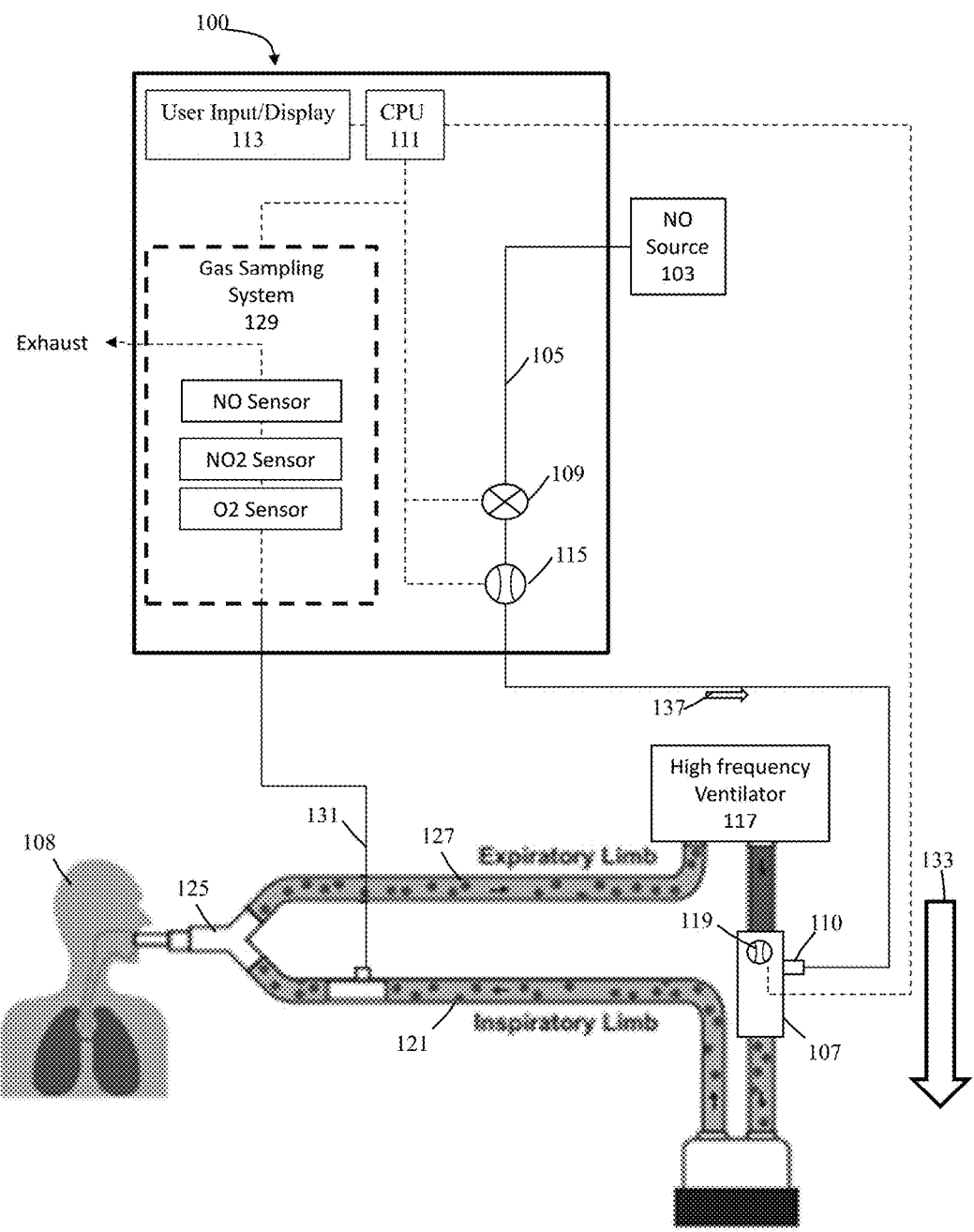
FIG. 1 illustratively depicts an exemplary nitric oxide delivery system, in accordance with exemplary embodiments of the present invention.

The present invention generally relates to systems and methods for delivery of therapeutic gas to patients, in need thereof, receiving breathing gas from a ventilator that can at least vary pressure and/or flow (e.g., high frequency ventilator, etc.) using, amongst other things, enhanced therapeutic gas (e.g., nitric oxide, NO, etc.) flow measurement. At least some of these enhanced therapeutic gas flow measurements can be used to address some surprising phenomenon that may, at times, occur when wild stream blending therapeutic gas into breathing gas that a patient receives from a breathing circuit affiliated with a ventilator that can at least vary pressure and/or flow (e.g., high frequency ventilator, etc.). Utilizing at least some of these enhanced therapeutic gas flow measurements and/or inventions herein the dose of therapeutic gas wild stream blended into breathing gas that the patient receives from the ventilator can be more accurate and/or under delivery of therapeutic gas into the breathing gas can be avoided and/or reduced.

As used herein, "wild stream blended proportional", "wild stream blending", "ratio metric blending" and the like, relates to stream blending, where the main flow stream is an uncontrolled (unregulated) stream that is referred to as the wild stream, and the component being introduced into the wild stream is controlled as a proportion of the main stream, which may typically be blended upstream (or alternatively downstream) of the main stream flowmeter. In various embodiments, the inspiratory flow may be the "wild stream" as the flow is not specifically regulated or controlled, and the nitric oxide is the blend component that is delivered as a percentage of the inspiratory flow through a delivery line.

As used herein, the term "false NO flow" and the like refers to flow phenomena that is inaccurately measured by flow sensors. Examples of such false NO flow include, but are not limited to, the measurement of NO flow by a flow sensor when NO is not actually flowing and the measurement of NO flow that is a significantly different value than the actual NO flow.

Systems and methods of the present invention can deliver therapeutic gas to a patient from a delivery system to an injector module, which in turn can be in fluid communication with a breathing circuit (affiliated with a ventilator such as, but not limited to, a high frequency ventilator and/or any other applicable ventilator and/or ventilation techniques) that the patient receives breathing gas from. Systems and methods of the present invention can include at least one therapeutic gas flow sensor that can measure the flow of therapeutic gas from the delivery system to the injector module, and in turn into the breathing circuit and to the patient. Advantageously, the therapeutic gas flow sensor can measure flow in more than one direction (e.g., bi-directional therapeutic gas flow sensor) and/or address some of the surprising phenomena that may, at times, occur when wild stream blending therapeutic gas into breathing gas in a breathing circuit affiliated with a ventilator that can at least vary pressure and/or flow (e.g., high frequency ventilator, etc.).

Further, systems and methods of the present invention can use techniques (e.g., algorithms, user input, etc.) to determine whether a ventilator that can at least vary pressure and/or flow (e.g., high frequency ventilator, etc.) may be being used and/or to compensate for at least some of the surprising phenomena that may, at times, occur when wild stream blending therapeutic gas into breathing gas in a breathing circuit affiliated with the ventilator. These techniques can, at times, use information from at least the therapeutic gas flow sensor that may measure flow in one direction (e.g., mono-directional flow sensor) and/or in more than one direction (e.g., bi-directional flow sensor).

Further still, systems and methods of the present invention can use techniques (e.g., algorithms, user input, etc.) to more effectively actuate valves and/or compensate for forces that may affect valve actuation such as, but not limited to, static friction, dynamic friction, and/or valve component interactions, to name a few. This can, in at least some instances, result in increased accuracy of NO delivery and monitoring and/or under delivery of therapeutic gas into the breathing gas can be avoided and/or reduced.

Referring to FIG. 1, illustratively depicted is an exemplary nitric oxide delivery system 100 for delivering therapeutic nitric oxide gas, via an injector module, to a patient receiving breathing gas from a high frequency ventilator. It will be understood that any teachings of the present invention can be used in any applicable system for delivering therapeutic gas to a patient receiving breathing gas from a breathing apparatus (e.g., ventilator, high frequency ventilator, breathing mask, nasal cannula, etc.). For example, systems and methods of the present invention can use, modify, and/or be affiliated with the delivery systems and/or other teachings of U.S. Pat. No. 5,558,083 entitled "Nitric Oxide Delivery System", the contents of which is incorporated herein by reference in its entirety.

Systems and methods of the present invention at times refer to use with a high frequency ventilator; however, systems and methods of the present invention can be used with any applicable breathing apparatus that may be affiliated with high frequency ventilation, any applicable breathing apparatus that may encounter like difficulties and/or problems, and/or any applicable breathing apparatus affiliated with ventilators and/or ventilation techniques (e.g., bi-level positive airway pressure, any ventilation technique varying pressure and/or flow, etc.) that can provide reverse inspiratory pressure and/or flow. Accordingly, reference to a high frequency ventilator is merely for ease and is in no way meant to be a limitation. Further, at times, inspiratory pressure and/or flow may not be reverse, rather there may be varying pressure and/or flow (e.g., high frequency sinusoidal pressure and/or flow) that can remain positive. For ease, reference made to reverse inspiratory pressure and/or flow, at times, encompasses situations when varying pressure and/or flow (e.g., high frequency sinusoidal pressure and/or flow) that can remain positive. Accordingly reference to reverse inspiratory pressure and/or flow is merely for ease and is in no way meant to be a limitation.

Systems and method of the present invention can be for use with any applicable therapeutic gas. The therapeutic gas, therapeutic gas flow measurements, therapeutic gas delivery system, and the like are, at times, described with reference to nitric oxide gas (NO) used for inhaled nitric oxide gas therapy. It will be understood that other therapeutic gases can be used. Accordingly, reference to nitric oxide, NO, and the like is merely for ease and is in no way meant to be a limitation.

Systems and methods of the present invention can be used to wild stream blend therapeutic gas into patient breathing gas in a breathing circuit and/or at any location. By way of example, therapeutic gas can be wild stream blended into patient breathing gas at a location prior to the breathing circuit. By way of another example, in at least some instances, the patient breathing circuit can include only one limb for both inspiratory and expiratory flow. For example, BiPAP ventilators can have only one limb that combines the inspiratory limb and expiratory limb. Following this example, therapeutic gas can be wild stream blended into patient breathing gas in the on limb that acts as both the inspiratory limb and expiratory limb. For ease, patient breathing circuits are, at times, depicted as having a separate inspiratory limb and expiratory limb. This is merely for ease and is in no way meant to be a limitation.

In exemplary embodiments, nitric oxide delivery systems such as nitric oxide delivery system 100 can be used to wild stream blend therapeutic gas (e.g., nitric oxide, NO, etc.) into patient breathing gas in a breathing circuit (affiliated with a high frequency ventilator) as a proportion of the patient breathing gas (e.g., ppm, etc.) and/or as a pulse (e.g., ml/breath, mg/kg/hr, etc.) To at least wild stream blend NO or pulse NO (e.g., which may also be wild stream blended as a pulse, etc.) into patient breathing gas, nitric oxide delivery system 100 can include and/or receive nitric oxide from a nitric oxide source 103 (e.g., cylinder storing NO, NO generator, etc.) for example, via a conduit 105. Instead of a cylinder of NO-containing gas, the NO may be generated bedside, such as by an appropriate chemical reaction, e.g. the reaction of a NO-releasing agent such as nitrogen dioxide with a reductant such as ascorbic acid. Further, conduit 105 can also be in fluid communication with an injector module 107, for example, via a therapeutic gas inlet 110, and injector module 107 can also be in fluid communication with an inspiratory limb of a breathing circuit affiliated with a high frequency ventilator 117.

As shown, high frequency ventilator 117 can include an inspiratory outlet for delivering breathing gas (e.g., forward flow 133) to the patient via an inspiratory limb 121 of a patient breathing circuit and an expiratory inlet for receiving patient expiration via an expiratory limb 127 of the patient breathing circuit. With injector module 107 coupled to inspiratory limb 121 of the breathing circuit, nitric oxide can be delivered from nitric oxide delivery system 100 (e.g., NO forward flow 137) to injector module 107, via conduit 105 and/or therapeutic gas inlet 110. This nitric oxide can then be delivered, via injector module 107, into inspiratory limb 121 of the patient breathing circuit affiliated high frequency ventilator 117 being used to delivery breathing gas to a patient 108.

To regulate flow of nitric oxide through conduit 105 to injector module 107, and in turn to a patient 108 receiving breathing gas from the patient breathing circuit, nitric oxide delivery system 100 can include one or more control valves 109 (e.g., proportional valves, binary valves, etc.). For example, with control valve 109 open, nitric oxide can be delivered to patient 108 by flowing in a forward direction (e.g., NO forward flow 137) through conduit 105 to injector module 107, and in turn to patient 108. For another example, with control valve 109 closed, nitric oxide may not be delivered to patient 108 as it may not flow in a forward direction.

In at least some instances, nitric oxide delivery system 100 can include one or more NO flow sensors 115 that can measure the flow of therapeutic gas (e.g., NO forward flow 137) through control valve 109 and/or conduit 105, in turn enabling measurement of the flow of therapeutic gas through a therapeutic gas inlet 110 into injector module 107, and in turn to patient 108. Further, in at least some instances, injector module 107 can include one or more breathing circuit gas (BCG) flow sensors 119 that can measure the flow of at least patient breathing gas (e.g., forward flow 133) through injector module 107, and in turn to patient 108. Although shown as being within injector module 107, BCG flow sensor 119 can be placed elsewhere in the inspiratory limb 121, such as upstream of the injector module 107. Also, instead of receiving flow information from BCG flow sensor 119, nitric oxide delivery system 100 may receive flow information directly from the high frequency ventilator 117 indicating the flow of breathing gas from high frequency ventilator 117.

In exemplary embodiments, systems and methods of the present invention can use, modify, and/or be affiliated with therapeutic gas delivery systems and methods which may have bi-directional breathing circuit gas (BCG) flow sensors. By way of example, the one or more breathing circuit gas (BCG) flow sensors 119 described herein may be bi-directional and/or systems and methods of the present invention can further include one or more bi-directional breathing circuit gas (BCG) flow sensors. For example, systems and methods of the present invention can use, modify, and/or be affiliated with the delivery systems and/or other teachings of U.S. patent application Ser. No. 14/672,447, filed Mar. 30, 2015 and entitled "SYSTEMS AND METHOD FOR DELIVERY OF THERAPEUTIC GAS TO PATIENTS IN NEED THEREOF USING ENHANCED BREATHING CIRCUIT GAS (BCG) FLOW MEASUREMENT", the contents of which is incorporated herein by reference in its entirety.

In exemplary embodiments, nitric oxide gas flow can be proportional (also known as ratio-metric) to the breathing gas flow to provide a desired concentration of NO in the combined breathing gas and therapeutic gas. For example, nitric oxide delivery system 100 can confirm that the desired concentration of NO is in the combined breathing gas and therapeutic gas by using the known NO concentration of NO source 103; the amount of breathing gas flow in the patient circuit using information from BCG flow sensor 119; and the amount of therapeutic gas flow in conduit 105 to injector module 107 (and in turn to patient 108) using information from NO flow sensor 115.

To at least deliver therapeutic gas to a patient and/or perform at least some teachings disclosed herein nitric oxide delivery system 100 can include a control system that can include one or more CPUs 111. CPU 111 can be coupled to a memory (not shown) and may be one or more of readily available memory such as random access memory (RAM), read only memory (ROM), flash memory, compact disc, floppy disk, hard disk, or any other form of local or remote digital storage. Support circuits (not shown) can be coupled to CPU 111 to support CPU 111, sensors, valves, sampling systems, user inputs/displays, injector modules, breathing apparatus, etc. in a conventional manner. These circuits can include cache, power supplies, clock circuits, input/output circuitry, subsystems, power controllers, signal conditioners, and the like. CPU 111 can be in communication with sensors, valves, sampling systems, user inputs/displays, injector modules, breathing apparatus, etc. In exemplary embodiments, the memory may store a set of machine-executable instructions (or algorithms), when executed by CPU 111, that can cause the delivery system to perform a method. For example, the delivery system can perform a method comprising: measuring flow in the inspiratory limb of a patient breathing circuit, delivering therapeutic gas containing nitric oxide to the patient during inspiratory flow, monitoring inspiratory flow or changes in the inspiratory flow, and varying the quantity (e.g. volume or mass) of therapeutic gas delivered in a subsequent inspiratory flow. The machine-executable instructions may also comprise instructions for any of the other methods described herein.

Further, to at least ensure accurate dosing of the therapeutic gas, nitric oxide delivery system 100 can include a user input/display 113 that can include a display and a keyboard and/or buttons, or may be a touchscreen device. User input/display 113 can receive desired settings from the user, such as the patient's prescription (in mg/kg ideal body weight, mg/kg/hr, mg/kg/breath, mL/breath, cylinder concentration, delivery concentration, duration, etc.), the patient's age, height, sex, weight, etc. User input/display 113 may also receive user input regarding the mode of operation, such as the use with a high frequency ventilator. For example, the user input/display 113 may have a button or other means for the user to indicate that the nitric oxide delivery device 100 is in use with a high frequency ventilator. User input/display 113 can in at least some instances be used to confirm patient dosing and/or gas measurements, for example, using a gas sampling system 129 that can receive samples of the gas being delivered to patient 108 via a sample line 131. Gas sampling system 129 can include numerous sensors such as, but not limited to, a nitric oxide gas sensor, a nitrogen dioxide gas sensor, and an oxygen gas sensor that can be used to display relevant information (e.g., gas concentrations, etc.) on user input/display 113.

Figure 2:
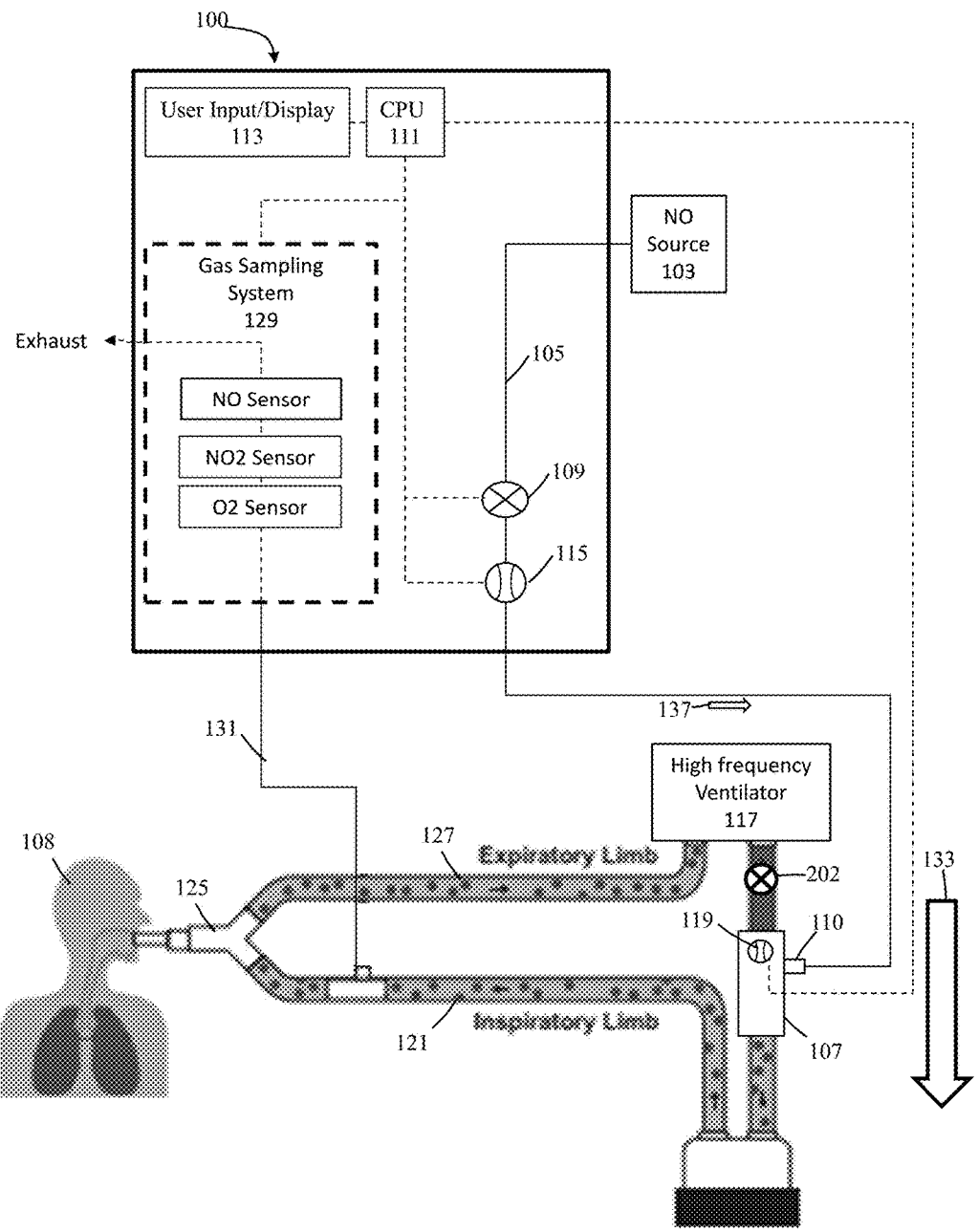
FIG. 2 illustratively depicts an exemplary nitric oxide delivery system including a check valve, in accordance with exemplary embodiments of the present invention.
Figure 3:
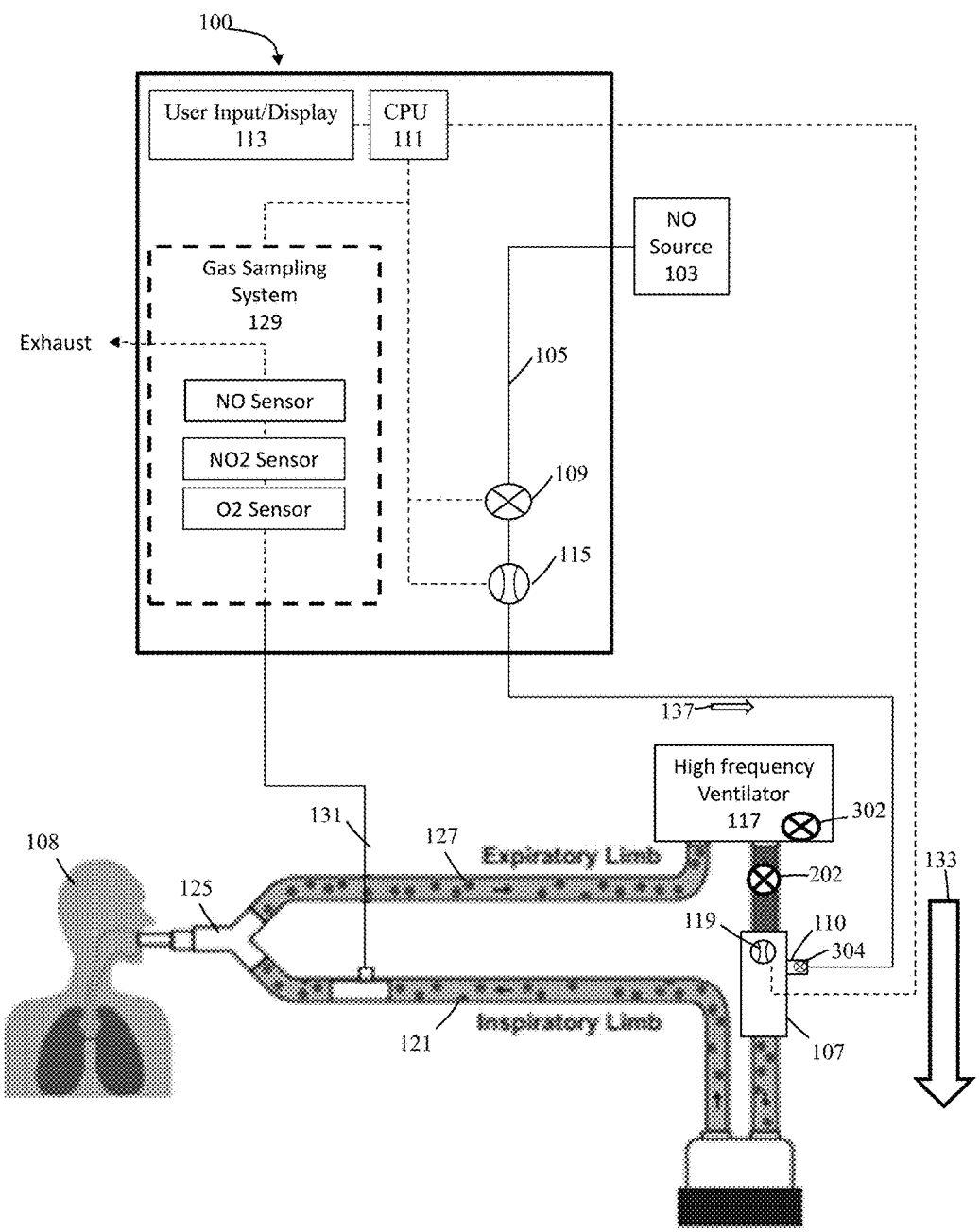
FIG. 3 illustratively depicts an exemplary nitric oxide delivery system used with an exemplary ventilator that includes a free breathing valve, in accordance with exemplary embodiments of the present invention.

As shown in FIGS. 1-3, the CPU 111 may be in communication with control valve 109, user input/display 113, NO flow sensor 115, BCG flow sensor 119 and/or gas sampling system 129. The CPU 111 may implement any of the methods described herein through the use of appropriate algorithms.

Although the above can be used beneficially to deliver therapeutic gas to a patient receiving breathing gas from a patient breathing circuit affiliated with a high frequency ventilator, the above can fail to take into account at least some surprising phenomena, for example, that may occur when wild stream blending NO into patient breathing gas as a percentage of the patient breathing gas. Without knowledge of at least some of these phenomena the actual NO concentration (e.g., NO concentration of the patient breathing gas, parts per million (PPM) NO, etc.) can be different (e.g., under dosed, etc.) from the desired NO concentration. This NO concentration can be particularly important as it can be the dosage of treatment for a patient. Accordingly, by taking into account at least some of these phenomena more accurate NO dosing can be possible and/or under dosing of NO can be avoided and/or reduced.

Extensive study discovered a phenomenon (false NO flow phenomenon) where, it was surprisingly found that wild stream blending NO with patient breathing gas in a breathing circuit affiliated with a high frequency ventilator, in at least some instances, can cause NO flow in the nitric oxide delivery line (e.g., conduit 105) and/or the injector module (e.g., therapeutic gas inlet 110) to be measured falsely as flowing by flow sensor 115 (even though NO may not be flowing). This can result in reduced accuracy of NO delivery and/or monitoring, for example, by NO delivery system 100 and/or this false NO flow can cause NO delivery system 100 to provide less NO than desired (e.g., under dose) as the system may falsely believe that the NO was provided.

These false NO flow measurements can be caused by vibrations or pressure oscillations caused by rapidly actuating valves and/or diaphragms (not shown) in high frequency ventilator 117 being registered as flow, for example, by flow sensor 115, which in turn NO delivery system 100 may use for NO delivery and/or monitoring. Flow can be falsely registered by flow sensor 115 because these vibrations or pressure oscillations may pressurize NO gas contained in conduit 105 for brief periods of time and when substantially small amounts of NO flow through conduit 105 this pressurization and/or depressurization (at times referred to simply as pressurization for ease) can result in the appearance of flow (e.g., NO forward flow 137) on NO flow sensor 115. This can result in situations where the nitric oxide delivery system falsely detects that NO forward flow 137 is occurring (e.g., in conduit 105, at injector module 107, through therapeutic gas inlet 110, etc.) when there may actually not be forward flow or flow at all. Accordingly, addressing at least this false flow phenomenon can result in increased accuracy of NO delivery and monitoring and/or under delivery of therapeutic gas into the breathing gas can be avoided and/or reduced.

Referring to FIG. 2, in exemplary embodiments, addressing at least false NO flow, a check valve 202 (e.g., a pneumatic check valve) can be placed in fluid communication with inspiratory limb 121. For example, check valve 202 can be placed so it is in fluid communication with inspiratory limb 121, while not be located at inspiratory limb 121. For another example, check valve 202 can be placed at inspiratory limb 121 upstream of injector module 107. In use, check valve 202 can open so sources of false NO flow, vibrations, and/or pressure oscillations can be diverted prior to reaching injector module 107 and/or being measured by flow sensor 115. Although the use of check valves can address at least some of the issues affiliated with false NO flow, these check valves can also introduce numerous problems such as, but not limited to, response flow lag from forward flow cracking pressure, surface seal and material electrostatic physical attraction to contamination affecting seal performance, unit to unit repeatability from component tolerance or material choice, surface finish affecting seal performance, characterized as an un-damped spring mass system vulnerable to producing audible noise or forward flow inducing oscillation "noise", and/or can detract from the overall flow control accuracy, repeatability, and control response time, to name a few.

Further, check valve 202 can interfere with high frequency ventilators that include a free breathing valve 302 as illustrated in FIG. 3. Free breathing valve 302 (sometimes called an anti-suffocation valve) can open to atmosphere should a patient using the ventilator spontaneously breath. Free breathing valve 302 can be required for ventilators to ensure that a patient who attempts to spontaneously breathe has the ability to inhale air. By way of example, if a ventilator does not include this free breathing valve it can be considered as a closed system with the ventilator being in control of when breathing air can be delivered to the patient. Without this free breathing valve, if a patient attempts to spontaneously breathe the user can be unable to pull in air to breathe as there can be no entrance for air to flow into the patient breathing circuit. With this free breathing valve, if a patient attempts to spontaneously breathe then the free breathing valve actuates enabling the user to pull in air from the surrounding environment. For ventilators that include free breathing valves, check valves included in the patient breathing circuit can defeat the purpose of this safety feature and may not be used with such ventilators.

In exemplary embodiments, to reduce and/or prevent interference with free breathing valve 302, check valve 202 and/or an additional check valve can be placed at, and/or be in fluid communication with, injector module 107, therapeutic gas inlet 110, and/or conduit 105. For example, at least one check valve 304, alone and/or in combination with check valve 202, can be located at therapeutic gas inlet 110 of injector module 107.

In exemplary embodiments, to address at least some of the above phenomena (e.g., false NO flow, etc.) and/or provide additional benefits, NO flow can be measured upstream of the control valve. In this configuration (e.g., the NO flow sensor upstream of the control valve), when the control valve is closed, the NO flow sensors exposure to at least some of the above phenomena can be substantially reduced and/or eliminated For example, to reduce and/or eliminate the NO flow sensors exposure to at least some of the above phenomena, NO flow sensor 115 can be located upstream of valve 109. In at least some instances, NO flow sensor 115, whether upstream or downstream of valve 109, can be used to determine whether valve 109 is working properly and/or whether flow is leaking past valve 109. For example, if flow beyond what is anticipated is detected by NO flow sensor 115 then this can be indicative of a leak in valve 109.

In exemplary embodiments, to address at least some of the above phenomena (e.g., false NO flow, etc.) and/or provide additional benefits, the NO delivery conduit (e.g., conduit 105) can have a substantially small cross-sectional diameter. For example, the NO delivery conduit (e.g., conduit 105) can have an internal cross-sectional diameter of about 1/32 of an inch to about 1/4 of an inch. For another example, the NO delivery conduit (e.g., conduit 105) can have an internal cross-sectional diameter of about 1/8 of an inch. The cross-section can be selected to substantially reduce the compressible volume in the NO delivery conduit, for example, so that the oscillatory signal detected by the flow sensor may be substantially reduced and/or effectively eliminated. In at least some instances, the cross-section can be selected to substantially increase resistance to flow so that pressure changes and/or oscillations affiliated with a high frequency ventilator may not be great enough to overcome the increased resistance to flow and/or so that propagation of the pressure changes and/or oscillations can be substantially reduced and/or eliminated, for example, prior to reaching the NO flow sensor (e.g., NO flow sensor affiliated with the delivery system, etc.). In at least some embodiments, the internal cross-sectional diameter of the NO delivery conduit (e.g., conduit 105) can be the same cross-sectional diameter whether internal or external to system 100 and/or NO delivery conduit (e.g., conduit 105) can be the same cross-sectional diameter at least once downstream of the flow control valve.

Figure 4A:
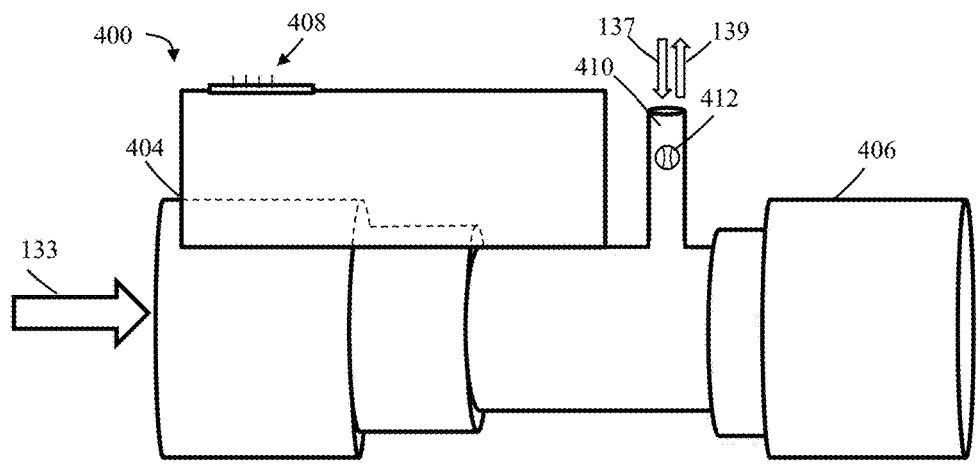
FIGS. 4A-4B illustratively depict an exemplary injector module that includes a bi-directional NO flow sensor, in accordance with exemplary embodiments of the present invention.
Figure 4B:
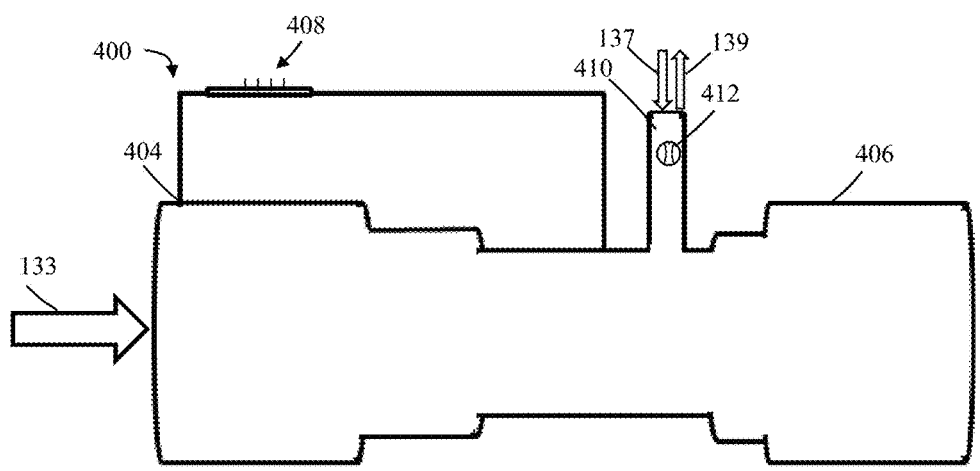

Referring to FIGS. 4A-4B, exemplary injector modules are illustratively depicted that can address at least some of the above phenomena (e.g., false NO flow, etc.) and/or provide additional benefits. Injector module 400 can include a first end 404 and a second end 406 that can be coupled to the inspiratory limb of the patient breathing circuit. At first end 404 and second end 406 there can be a first opening and a second opening, respectively, in the body of injector module 400 enabling fluid flow (e.g., breathing gas, etc.) through the injector module. Injector module 400 can also include a communication port 408 enabling communication of information between the injector module (and any affiliated components) and the nitric oxide delivery system (e.g., fluid and/or pneumatic communication, electrical and/or digital communication, etc.). Systems and methods of the present invention may use this information to, for example, address at least some of the above described phenomena and/or provide additional benefits. Further, injector module 400 can include a therapeutic gas inlet 410 that can receive therapeutic gas from the nitric oxide delivery system and/or can enable injection of therapeutic gas into breathing gas flowing through the injector module.

In exemplary embodiments, injector modules of the current invention can include and/or be in fluid communication with one or more bi-directional NO flow sensors, for example, to address at least some of the above phenomena (e.g., false NO flow, etc.) and/or provide additional benefits. For example, injector module 400 can include and/or be in fluid communication with one or more bi-directional nitric oxide (NO) flow sensors 412. Bi-directional NO flow sensor 412 can be located at and/or be in fluid communication with therapeutic gas inlet 410 and/or bi-directional NO flow sensor 412 can measure flow through the NO delivery conduit (e.g., conduit 105 illustrated in FIG. 1) to injector module 400 and/or to the inspiratory limb of the patient breathing circuit. Further, bi-directional NO flow sensor 412 can be used as a feedback control signal for NO delivery and/or can be used to monitor the flow and/or quantity of NO gas being delivered into the patient breathing circuit. For example, flow measurements from bi-directional NO flow sensor 412 can be compared against flow measurements from flow sensor 115 to detect NO leaks. This can result in more accurate dosing and/or can reduce the risk of nitric oxide leaking into the surrounding environment.

In at least some embodiments, although illustrated as being located at therapeutic gas inlet 410, bi-directional NO flow sensor 412 can be in any location in fluid communication with NO being delivered to the injector module. For example, bi-directional NO flow sensor 412 can be located at the nitric oxide delivery system and/or at any point that can be in fluid communication with the NO delivery conduit (e.g., conduit 105 illustrated in FIG. 1). For another example, bi-directional NO flow sensor 412 can replace, or be used in conjunction with, NO flow sensor 115 (illustrated in FIGS. 1-3).

In at least some embodiments, two or more bi-directional NO flow sensors can be located at and/or be in fluid communication with therapeutic gas inlet 410. For example, one or more bi-directional NO flow sensors can be located at therapeutic gas inlet 410 and/or one or more bi-directional NO flow sensors can be in fluid communication with therapeutic gas inlet 410. Two or more bi-directional NO flow sensors can, for example, enable flow measurements of NO being delivered via injection module 400 for a substantially wide range of flow rates.

In exemplary embodiments, bi-directional NO flow sensor 412 can be any sensor capable of measuring flow in both the forward and reverse direction For example, bi-directional flow sensor 119 can be a thermal mass flow meter (sometimes called a thermal dispersion flow meter); pressure-based flow meter; optical flow meter; electromagnetic, ultrasonic, and/or Coriolis flow meter; laser Doppler flow meter, and/or any flow meter that provides a response time of less than about two milliseconds and has a range of not more than +−10 SLPM. Exemplary limits for the reverse flow may be −10, −9, −8, −7, −6, −5, −4, −3, −2.5, −2, −1.5, −1, −0.75, −0.5, −0.4, −0.3, −0.2 or −0.1 SPLM. Similarly, exemplary limits for the forward flow may be 10, 9, 8, 7, 6, 5, 4, 3, 2.5, 2, 1.5, 1, 0.75, 0.5, 0.4, 0.3, 0.2 or 0.1 SPLM. In at least some instances, bi-directional flow sensor 119 can be a pressure-based flow meter (e.g., differential pressure sensor type flow meter, etc.) and/or fluid and/or pneumatic communication can be provided via communications port 408.

In exemplary embodiments, bi-directional NO flow sensor 412 can be in communication with the nitric oxide delivery system, for example, via communication port 408. This can allow flow information to be communicated to the nitric oxide delivery system, which can be used by the nitric oxide delivery system for NO delivery and/or monitoring. Using this bi-directional flow information nitric oxide delivery system can more accurately deliver and/or monitor NO.

In exemplary embodiments, systems and methods of the present invention can use techniques (e.g., algorithms, user input, etc.) to determine whether a high frequency ventilator may be being used. Further, in exemplary embodiments, if determined that a high frequency ventilator may be being used, systems and methods of the present invention can use techniques (e.g., algorithms, user input, etc.) to compensate for at least some of the surprising phenomena (e.g., false NO flow, etc.) and/or affects that may, at times, occur when wild stream blending therapeutic gas into breathing gas in a breathing circuit affiliated with a high frequency ventilator and/or provide additional benefits. These techniques can, at times, use information from at least the therapeutic gas flow sensor, such as, NO flow sensor 115 (e.g., that may measure flow in one direction, etc.), NO flow sensor 412 (e.g., that may measure flow in more than one direction, etc.) and/or any flow sensor in fluid communication with, the injector module, the therapeutic gas inlet, and/or the NO conduit.

Systems and methods of the present invention can determine whether or not therapeutic gas (e.g., NO) may be being delivered into a breathing circuit affiliated with a high frequency ventilator using any reasonable technique, such as, but not limited to, user input (e.g., user input information to the nitric oxide delivery system), detection (e.g., detection algorithm by the nitric oxide delivery system), signal recovery, and/or any combination and/or further separation thereof, direct communication with the ventilator, to name a few. For example, the nitric oxide delivery system can allow a user to input that NO may be being delivered into a breathing circuit affiliated with a high frequency ventilator. For another example, the nitric oxide delivery system can detect (e.g., without user input, with some user input, etc.) that NO may be being delivered into a breathing circuit affiliated with a high frequency ventilator using, for example, detection and/or signal recovery techniques.

In exemplary embodiments, if determined that a high frequency ventilator may be being used, systems and methods of the present invention can compensate for at least some of the surprising phenomena (e.g., false NO flow phenomena, etc.), effects affiliated with high frequency ventilators, and/or provide additional benefits using any reasonable technique, such as, but not limited to, filtering, using reduction techniques, any combination and/or further separation thereof, and/or using any process capable of compensating for high frequency ventilator generated information affiliated with NO flow information, changing the NO delivery control algorithm such that it may not respond to high frequency oscillations, electrical filtering, digital filtering, the NO flow sensor being located upstream of the flow control valve, substantially small diameter NO injection tubing being used, and/or pneumatic filtering, to name a few. By way of example, systems and methods of the present invention can consider high frequency ventilator generated information as noise and can use any reasonable technique to remove this noise from the NO flow information (e.g., information from the NO flow sensor). Techniques can include, but are not limited to, linear filters, nonlinear filters, statistical signal processing, noise gating, and/or any combination and/or further separation thereof, to name a few.

To ease understanding, at least some exemplary detection and/or signal recovery techniques and/or exemplary compensation techniques are disclosed herein. It will be understood that other techniques can be used. Further, it will be understood that techniques disclosed herein are merely for ease of understanding and are in no way meant to be exhaustive.

By way of example, to determine whether NO may be being delivered into a breathing circuit affiliated with a high frequency ventilator, systems and methods of the present invention can identify pressure and/or flow information indicative of use of high frequency ventilator systems. In at least some instances pressure and/or flow information from an NO flow sensor, such as, flow sensor 115 (illustrated in FIGS. 1-3) and/or bi-directional NO flow sensor 412 (illustrated in FIGS. 4A-4B) can be analyzed (e.g., by the nitric oxide delivery system) to determine if a high frequency ventilator may be being used. For example, information from the NO flow sensor may be analyzed against expected information from the NO flow sensor and/or actual NO flow information may be discerned from high frequency ventilator generated flow information that distracts from the actual NO flow information. By way of example, information from NO flow sensor indicative high frequency unexpected forward and/or reverse flow and/or pressure, high frequency unexpected forward flow and/or pressure, high frequency unexpected zero and/or forward and/or reverse flow, to name a few, can be analyzed against expected flow information.

Figure 5A:
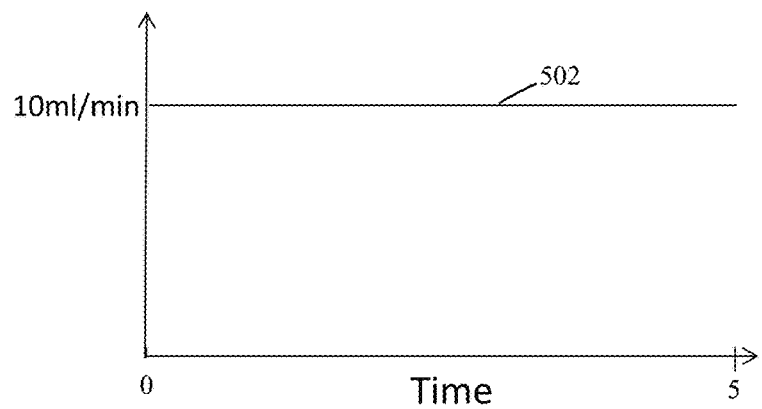
FIGS. 5A-5C illustratively depict exemplary graphical representations of information from flow sensors, in accordance with exemplary embodiments of the present invention.
Figure 5B:
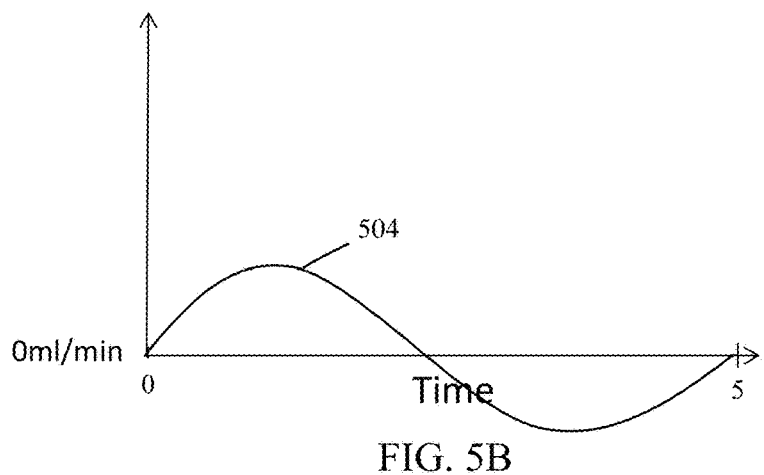
Figure 5C:
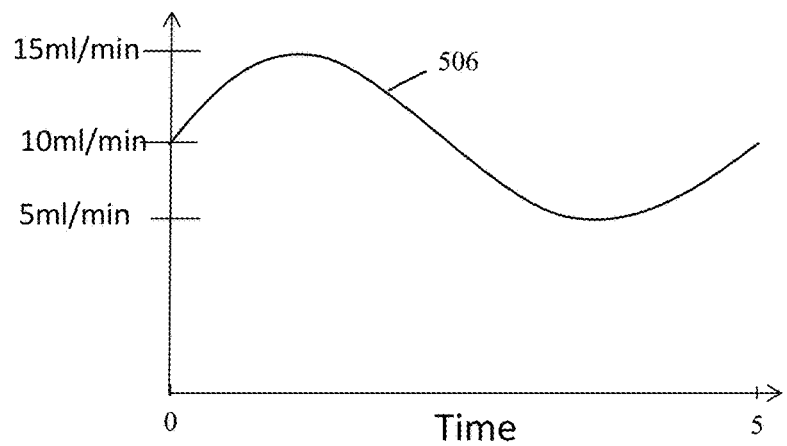

Referring to FIGS. 5A-5C graphical representation of information from an NO flow sensor are illustratively depicted to demonstrate at least one exemplary technique for determining if a high frequency ventilator may be being used. It will be understood that information from the NO flow sensor may be in the form of a current, voltage, and/or any other form of information that may be indicative of a flow and/or pressure. For ease, the indicative flow rate is illustratively depicted. This is merely for ease and is in no way meant to be a limitation.

Referring to FIG. 5A, plot 502 illustratively depicts exemplary expected information from the NO flow sensor for a desired flow rate of 10 ml/min, for example, when delivering NO into a breathing circuit that may not be affiliated with a high frequency ventilator. Plot 502, as illustrated, can be considered to be a substantially flat line as plot 502 illustrates the expected information from the NO flow sensor for a constant flow rate (e.g., constant flow rate of 10 ml/min). Of course should the flow rate not be constant the plot would correspond accordingly. For example, a constant flow rate may be provided for a portion of a patient's breathing cycle and then varied for another portion of the patient's breathing cycle. For ease of understanding a constant flow rate is illustrated. This is merely for ease and is in no way meant to be a limitation.

Referring to FIG. 5B, plot 504 illustratively depicts exemplary high frequency ventilator expected information from the NO flow sensor for an exemplary flow rate of 0 ml/min. Plot 504, as illustrated, can be considered to be a non-linear shape (e.g., sinusoidal, etc.) as plot 504 illustrates information from the NO flow sensor for vibrations or pressure oscillations, for example, that may be at least partially generated by the high frequency ventilator.

Referring to FIG. 5C, plot 506 illustratively depicts exemplary actual information from the NO flow sensor for a flow rate of 10 ml/min when distorted by vibrations or pressure oscillations. Plot 506 can, at times, be considered to be the distorted sum of the exemplary expected information from the NO flow sensor for a desired flow rate of 10 ml/min (e.g., plot 502 in FIG. 5A) combined with exemplary information from the NO flow sensor indicative of high frequency ventilator generated vibration or pressure oscillations. These distortions can cause the nitric oxide delivery system to believe flow may be being delivered at a rate other than the desired constant flow rate of 10 ml/min (even though these distortions may be indicative of false NO flow and not the actual NO flow).

Problematically, in response to this incorrect flow information, the NO delivery system may adjust the flow of gas to the breathing circuit to attempt to deliver at the desired flow rate. As this new flow rate may be based on distortions and not the actual flow rate this adjusted flow rate can cause the actual delivery of NO into the breathing circuit to not be at the desired flow rate.

Even further compounded the above problem, as the NO delivery system attempts to adjust the flow of gas to the breathing circuit to attempt to deliver at the desired flow rate, the delivery valve(s) (e.g., valve 109, etc.) may be actuated (e.g., opened, closed, partially opened, partially closed, etc.). This valve actuation may cause interaction of the valve components which can, in at least some instances, cause at least a lag time in delivery. By way of example, when attempting to adjust the flow (which may not need to be adjusted) the valve may be closed and then reopened requiring the valve to overcome forces affiliated with static friction and/or dynamic friction. These forces may not be constant (e.g., more force may be required to overcome static friction than dynamic friction) which can cause a lag in valve actuation and/or NO delivery. In exemplary embodiments, using techniques disclosed herein the quantity of times that the system attempts to adjust the NO flow may be reduced and/or eliminated. This can result in reducing the incidence of the above disclosed problem. Further, this can, in at least some instances, result in increased accuracy of NO delivery and monitoring and/or under delivery of therapeutic gas into the breathing gas can be avoided and/or reduced.

Addressing at least the above, in exemplary embodiments, systems and methods of the present invention can use techniques (e.g., algorithms, user input, etc.) to more effectively actuate valves and/or compensate for forces that may affect valve actuation such as, but not limited to, static friction, dynamic friction, and/or valve component interactions, to name a few. For example, systems and methods of the present invention may, at times, identify, factor in, and/or compensate for the amount of force needed to overcome various forces (e.g., static friction, dynamic friction, etc.).

Still referring to FIGS. 5A-5C, following the above example, to detect use of a high frequency ventilator, systems and methods of the present invention can analyze the actual information from the NO flow sensor against the expected information from the NO flow sensor for a desired flow rate. For example, when delivering 10 ml/min of NO the nitric oxide delivery system analyzes actual information from the NO flow sensor (e.g., as illustrated in plot 506 of FIG. 5C) against expected information from the NO flow sensor (e.g., as illustrated in plot 502 of FIG. 5A) and identifies substantial deviation then the nitric oxide delivery system can determine that NO may be being delivered into a breathing circuit affiliated with a high frequency ventilator. Substantial deviations may be identifiable as flow oscillations of less than about 80 oscillations per minute can be expected as conventional ventilator breath rates can be less than about 80 breaths per minute while oscillations affiliated with high frequency ventilators can be on the magnitude of hundreds of oscillations per minute.

Still following the above example, with use of a high frequency ventilator being detected, systems and methods of the present invention can compensate for the information generated by at least the high frequency ventilator. For example, the nitric oxide delivery system can filter out information indicative of high frequency ventilator generated vibration or pressure oscillations from the information from the NO flow. With this high frequency generated information filtered out, the nitric oxide delivery system can deliver the correct dose of NO to the patient.

Compounding the above challenges, it has been found that at least the above false NO flow phenomena can, at times, be more likely for substantially small flow rates (e.g., less 100 ml/min). Further, at least the above phenomena can distort the flow information to a large enough degree that zero flow and/or negative flow may be believed to be occurring. Problematically, substantially small flow rates may be beneficial and/or required to deliver the desired dose of NO to a patient. Failure to detect and/or compensate for at least the above phenomena may, at times, lead to delivery of dosing to a patient that may not be the desired therapeutic dose and, this may, at times, impact efficacy.

In exemplary embodiments, smaller distortions may be compensated for using information from a mono-directional and/or bi-directional flow sensor and/or larger distortions may, at times, require using information from a bi-directional flow sensor and/or may require additional techniques. Referring back to FIG. 5C, plot 506 shows a distortion of the desired 10 ml/min flow as being between 5 ml/min and 15 ml/min. Under this example, detection and/or compensation for false NO flow may be accomplished by a mono-directional flow sensor and/or bi-directional flow sensor, for example, as the flow rate does not go below 0 ml/min. However, in exemplary embodiments, for distortions of the desired flow below 0 ml/min detection and/or compensation can be more complicated and/or require a bi-directional flow sensor.

Figure 6A:
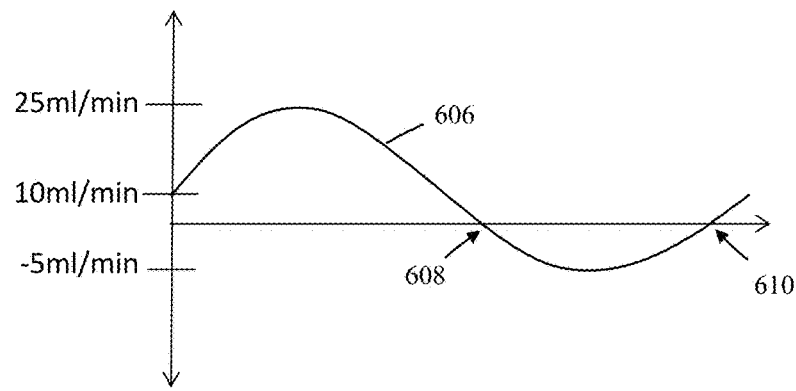
FIGS. 6A-6C illustratively depict exemplary graphical representations of information from flow sensors that include information and/or representations indicative of negative flow, in accordance with exemplary embodiments of the present invention.

For example, referring to FIG. 6A, plot 606 shows a 10 ml/min desired flow exhibiting 15 ml/min distortions (e.g., plot 606 distorts between 25 ml/min and −5 ml/min) such that the desired flow distorts below 0 ml/min between points 608 and 610. This negative region of plot 606 between points 608 and 610 can be considered to be indicative of false NO flow in the reverse direction. As this flow may be considered to be in the reverse direction, using bi-directional flow sensor information plot 606 may appear as shown in FIG. 6A while using mono-directional flow sensor information plot 606 may appear as shown in FIG. 6B (e.g., as no flow, 0 ml/min flow, etc.) and/or as shown in FIG. 6C (e.g., as an equal and opposite positive flow, as positive values for the negative values).

In exemplary embodiments, a bi-directional flow sensor and/or information from a bi-directional flow sensor may be used to detect and/or compensate for substantially small flows and/or distortions indicative of flow below 0 ml/min. Information from a bi-directional flow sensor may be used to detect use of a high frequency ventilator and/or may be used to compensate for information from the NO flow sensor that may be indicative of high frequency ventilator generated vibration or pressure oscillations using any reasonable technique such as, but not limited to, any of the techniques disclosed herein.

Figure 6B:
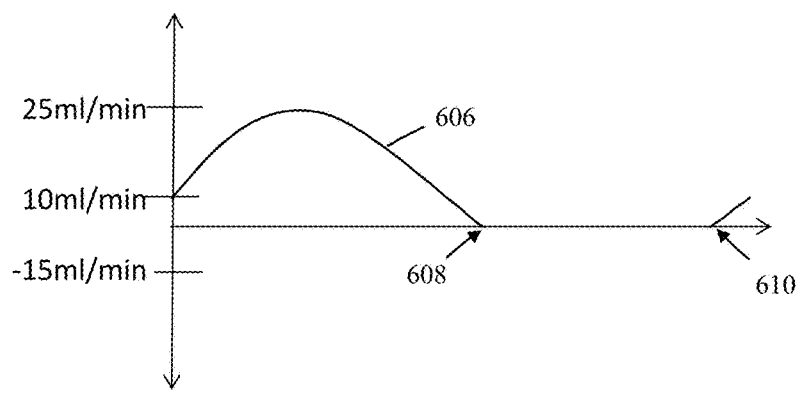
Figure 6C:
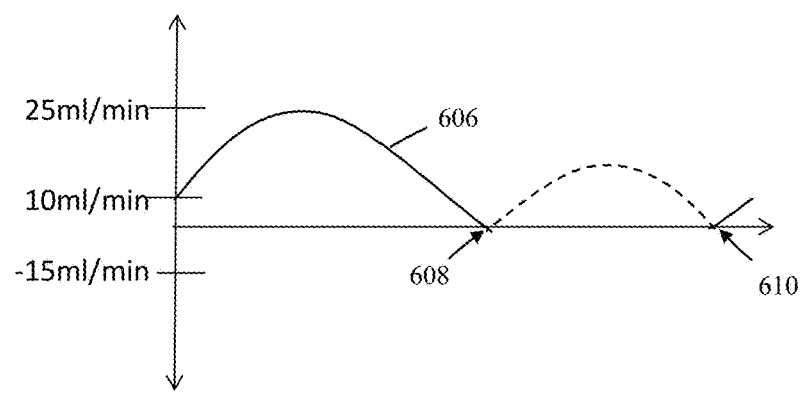

Referring to FIGS. 6B-6C, in exemplary embodiments, a mono-directional flow sensor and/or information from a mono-directional flow sensor may be used to detect and/or compensate for substantially small flows and/or distortions indicative of flow below 0 ml/min using any reasonable technique, such as, but not limited to, interpolation, curve fitting, and/or regression analysis, to name a few.

For example, to detect use of a high frequency ventilator using a mono-directional flow sensor and/or information from a mono-directional flow sensor, systems and methods of the present invention can analyze the actual information from the NO flow sensor against the expected information from the NO flow sensor for a desired flow rate and may consider distortions above the expected information from the NO flow sensor. Using this technique, system and methods of the present invention may detect use of a high frequency ventilator by only considering positive values above the expected information from the NO flow sensor using any reasonable technique such as, but not limited to, any of the techniques disclosed herein.

Following the above example, with use of a high frequency ventilator being detected using a mono-directional flow sensor and/or information from a mono-directional flow sensor, systems and methods of the present invention can compensate for information that may be indicative of high frequency ventilator generated vibration or pressure oscillations using any reasonable technique such as, but not limited to, any of the techniques disclosed herein. For example, for the region between points 608 and 610 of plot 606 (as shown in FIG. 6B), systems and methods of the present invention can interpolate the missing plot information and compensate for the distortions (e.g., distortions actually seen and/or interpolated distortions) using any reasonable technique such as, but not limited to, any of the techniques disclosed herein. For another example, for the region between points 608 and 610 of plot 606 (as shown in FIG. 6C), systems and methods of the present invention can invert these values (e.g., consider the positive values as negative values) and compensate for the distortions (e.g., distortions actually seen and/or inverted distortions) using any reasonable technique such as, but not limited to, any of the techniques disclosed herein.

Those skilled in the art will readily recognize numerous adaptations and modifications which can be made to the therapeutic gas delivery systems and method of delivering a pharmaceutical gas of the present invention which will result in an improved method and system for introducing a known desired quantity of a pharmaceutical gas into a patient, yet all of which will fall within the scope and spirit of the present invention as defined in the following claims. Accordingly, the invention is to be limited only by the following claims and their equivalents.

Reference throughout this specification to "one embodiment," "certain embodiments," "one or more embodiments," "exemplary embodiment," "exemplary embodiments," and/or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment," "exemplary embodiment," "exemplary embodiments," and/or "in an embodiment" in various places throughout this specification are not necessarily referring to the same embodiment of the invention. Furthermore, the particular features, structures, materials, or characteristics can be combined in any suitable manner in one or more embodiments.

It will be understood that any of the steps described can be rearranged, separated, and/or combined without deviated from the scope of the invention. For ease, steps are, at times, presented sequentially. This is merely for ease and is in no way meant to be a limitation.

Further, it will be understood that any of the elements and/or embodiments of the invention described can be rearranged, separated, and/or combined without deviated from the scope of the invention. For ease, various elements are described, at times, separately. This is merely for ease and is in no way meant to be a limitation.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A nitric oxide delivery system for delivering therapeutic gas into breathing gas in the inspiratory limb of a patient breathing circuit affiliated with a high frequency ventilator or ventilation techniques which provide reverse and/or oscillations in inspiratory pressure or flow, the nitric oxide delivery system comprising:
   at least one control valve for providing a flow of therapeutic gas;
   an injector module comprising:
      an injector body having a first opening and a second opening, the first opening and the second opening being configured to couple the injector module to the inspiratory limb of a breathing circuit enabling patient breathing gas in the breathing circuit to flow through the first opening and second opening;
      a therapeutic gas inlet in the injector body, the therapeutic gas inlet being configured to receive the flow of therapeutic gas and enable injection of the therapeutic gas into the injector module, and in turn into patient breathing gas in the inspiratory limb of the breathing circuit;
   at least one NO flow sensor in fluid communication with the therapeutic gas inlet; and
   a control system in communication with the at least one NO flow sensor to receive flow information from the at least one NO flow sensor, wherein the control system:
      (i) detects use of the high frequency ventilator;
      (ii) compensates for false NO flow phenomenon by treating flow information generated by the high frequency ventilator as noise and filtering this noise out and/or using noise reduction techniques;
      (iii) identifies flow information as missing and interpolates the missing flow information and/or
      (iv) identifies flow information as reverse flow and inverts the value of the flow information.

2. The nitric oxide delivery system of claim 1, wherein the control system detects false NO flow phenomenon by analyzing user input information, using a noise detection algorithm, and/or signal recovery algorithm.

3. The nitric oxide delivery system of claim 1, wherein the control system uses the flow information to ensure that the desired dose of NO is delivered into the injector module, and in turn into patient breathing gas in the inspiratory limb of the breathing circuit.

4. The nitric oxide delivery system of claim 1, wherein the control system uses the flow information to ensure that the desired dose of NO is not under delivered and/or under dosed.

5. The nitric oxide delivery system of claim 1, further comprising a check valve that is one or more of (i) in fluid communication with the therapeutic gas inlet of the injector module and (ii) is integral to the injector module.

6. The nitric oxide delivery system of claim 1, wherein the at least one bi-directional flow sensor is a thermal mass flow meter (thermal dispersion flow meter).

7. The nitric oxide delivery system of claim 1, wherein the inspiratory limb is also an expiratory limb in the breathing circuit.

8. The nitric oxide delivery system of claim 1, wherein the therapeutic gas comprises one or more of (i) nitric oxide and (ii) a nitric-oxide releasing agent.

9. The nitric oxide delivery system of claim 1, wherein the control valve is upstream of the NO flow sensor.

10. The nitric oxide delivery system of claim 1, wherein the therapeutic gas inlet receives the flow of therapeutic gas via a conduit, and the conduit one or more of (i) has internal cross-sectional diameter of about 1/32 of an inch to about 1/4 of an inch and (ii) has an internal portion within the nitric oxide delivery system and an external portion outside the nitric oxide delivery system, the internal portion of the conduit having a cross-sectional diameter that is substantially the same as a cross-sectional diameter of the external portion of the conduit.

11. The nitric oxide delivery system of claim 1, further comprising at least a second NO flow sensor in fluid communication with the therapeutic gas inlet and in communication with the control system, wherein the control system receives flow information from the NO flow sensors and detects a leak when the flow information from the NO flow sensors does not match.

12. The nitric oxide delivery system of claim 11, wherein the flow of therapeutic gas is increased if a leak is detected.

13. A nitric oxide delivery system for delivering therapeutic gas into breathing gas in the inspiratory limb of a patient breathing circuit affiliated with a high frequency ventilator or ventilation techniques which provide reverse and/or oscillations in inspiratory pressure or flow, the nitric oxide delivery system comprising:
at least one control valve for providing a flow of therapeutic gas;
an injector module comprising:
an injector body having a first opening and a second opening, the first opening and the second opening being configured to couple the injector module to the inspiratory limb of a breathing circuit enabling patient breathing gas in the breathing circuit to flow through the first opening and second opening;
a therapeutic gas inlet in the injector body, the therapeutic gas inlet being configured to receive the flow of therapeutic gas and enable injection of the therapeutic gas into the injector module, and in turn into patient breathing gas in the inspiratory limb of the breathing circuit;
at least one bi-directional NO flow sensor in fluid communication with the therapeutic gas inlet, the at least one bi-directional NO flow sensor being capable of measuring flow in a forward direction and in a reverse direction through the therapeutic gas inlet; and
a control system in communication with the at least one bi-directional NO flow sensor to receive bi-directional flow information comprising at least forward flow information and reverse flow information from the at least one bi-directional NO flow sensor.

14. The nitric oxide delivery system of claim 13, wherein the control system detects false NO flow phenomenon by analyzing user input, detection algorithm, and/or signal recovery.

15. The nitric oxide delivery system of claim 13 wherein the control system uses the bi-directional flow information to compensate for false NO flow phenomenon by treating flow information generated by the high frequency ventilator as noise and filtering this noise out and/or using noise reduction techniques.

16. The nitric oxide delivery system of claim 13, wherein the control system uses the bi-directional flow information to ensure that the desired dose of NO is delivered into the injector module, and in turn into patient breathing gas in the inspiratory limb of the breathing circuit.

17. The nitric oxide delivery system of claim 13, wherein the control system uses the bi-directional flow information to ensure that the desired dose of NO is not under delivered and/or under dosed.

18. The nitric oxide delivery system of claim 13, further comprising a check valve that is one or more of (i) in fluid communication with the therapeutic gas inlet of the injector module and (ii) is integral to the injector module.

19. The nitric oxide delivery system of claim 13, wherein the at least one bi-directional flow sensor is a thermal mass flow meter.

20. The nitric oxide delivery system of claim 13, wherein the inspiratory limb is also an expiratory limb in the breathing circuit.

21. The nitric oxide delivery system of claim 13, wherein the therapeutic gas comprises one or more of (i) nitric oxide and (ii) a nitric-oxide releasing agent.

22. The nitric oxide delivery system of claim 13, wherein the control valve is upstream of the NO flow sensor.

23. The nitric oxide delivery system of claim 13, wherein the therapeutic gas inlet receives the flow of therapeutic gas via a conduit, and the conduit one or more of (i) has internal cross-sectional diameter of about 1/32 of an inch to about 1/4 of an inch and (ii) has an internal portion within the nitric oxide delivery system and an external portion outside the nitric oxide delivery system, the internal portion of the conduit having a cross-sectional diameter that is substantially the same as a cross-sectional diameter of the external portion of the conduit.

24. The nitric oxide delivery system of claim 13, further comprising at least a second NO flow sensor in fluid communication with the therapeutic gas inlet and in communication with the control system, wherein the control system receives flow information from the NO flow sensors and detects a leak when the flow information from the NO flow sensors does not match.

25. The nitric oxide delivery system of claim 24, wherein the flow of therapeutic gas is increased if a leak is detected.

* * * * *